(12) United States Patent
Zheng et al.

(10) Patent No.: US 9,309,547 B2
(45) Date of Patent: Apr. 12, 2016

(54) METHODS FOR MAKING TOCOFLEXOLS AND ANALOGUES THEREOF

(71) Applicants: The Board of Trustees of the University of Arkansas, Little Rock, AR (US); The United States of America as Represented by the Department of Veterans Affairs, Washington, DC (US)

(72) Inventors: Guangrong Zheng, Little Rock, AR (US); Cesar Compadre, Little Rock, AR (US); Martin Hauer-Jensen, Little Rock, AR (US); Peter Crooks, Little Rock, AR (US); Philip Breen, Little Rock, AR (US)

(73) Assignees: THE BOARD OF TRUSTEES OF THE UNIVERSITY OF ARKANSAS, Little Rock, AR (US); THE UNITED STATES OF AMERICA, AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 14/402,792

(22) PCT Filed: Mar. 13, 2013

(86) PCT No.: PCT/US2013/030862
§ 371 (c)(1),
(2) Date: Nov. 21, 2014

(87) PCT Pub. No.: WO2013/176745
PCT Pub. Date: Nov. 28, 2013

(65) Prior Publication Data
US 2015/0087033 A1    Mar. 26, 2015

Related U.S. Application Data

(60) Provisional application No. 61/650,021, filed on May 22, 2012.

(51) Int. Cl.
*C12P 17/06* (2006.01)
*C07D 311/58* (2006.01)

(52) U.S. Cl.
CPC ............... *C12P 17/06* (2013.01); *C07D 311/58* (2013.01)

(58) Field of Classification Search
CPC .............................. C07D 311/58; C12P 17/06
See application file for complete search history.

(56) References Cited

FOREIGN PATENT DOCUMENTS

WO    WO2011/153353    * 12/2011

\* cited by examiner

*Primary Examiner* — Valerie Rodriguez-Garcia
(74) *Attorney, Agent, or Firm* — Andrus Intellectual Property Law, LLP

(57) ABSTRACT

Methods for the synthesis of tocoflexols of Formula (I) and (II) and a number of related tocol analogs are provided herein. The methods are economical and amenable to large scale production and can be performed using either pure of partially purified tocotrienols as the starting material.

13 Claims, 2 Drawing Sheets

METHODS FOR MAKING TOCOFLEXOLS AND ANALOGUES THEREOF

CROSS-REFERENCE TO RELATED APPLICATIONS

This patent application is a national stage filing under 35 U.S.C. 371 of International Application No. PCT/US2013/30862, filed Mar. 13, 2013, which claims the benefit of priority of U.S. Provisional Patent Application No. 61/650,021, flied May 22, 2012, both of which are incorporated herein by reference in their entirety.

STATEMENT REGARDING FEDERALLY SPONSORED RESEARCH

This invention was made with United States government support awarded by the National Institutes of Health, National Center for Research Resources, award 1UL1RR029884 and National Institutes of Health grant number 5R01CA083719-10. The United States has certain rights in this invention.

FIELD OF THE INVENTION

The present invention relates to methods for the synthesis of tocoflexols of formula (I) and (II) and a number of related tocol analogues.

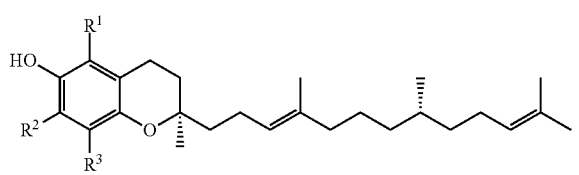

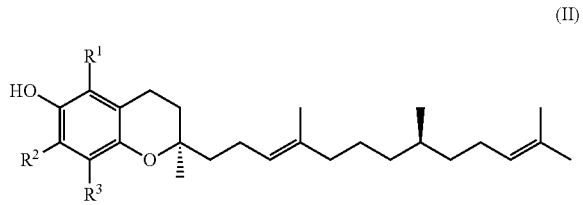

BACKGROUND

The tocols are known to have beneficial health effects when provided as a dietary supplement. Efficient transport out of the liver is necessary for the tocols to deliver the beneficial health effects. The tocols are transported out of the liver and into the blood stream by a protein called αTTP (tocopherol transfer protein). Some tocols, specifically the tocopherols, are more efficiently transported out of the liver and into the blood stream than the tocotrienols and have a longer half-life in the body due to their higher binding affinity to αTTP than their tocotrienol counterparts.

The tocotrienols have recently been shown to have some beneficial health effects not seen with the tocopherols. However, their limited half-life in the body greatly reduces their bioavailability, and limits their usefulness. Provided herein are methods of making tocol derivatives with modifications to the hydrocarbon tail to allow more efficient binding and uptake of tocols with unsaturated hydrocarbon tails by αTTP. The derivatives were named tocoflexols to indicate the increased flexibility of the hydrocarbon tail as compared to the tails of tocotrienols and differentiate this class of compounds from the tocopherols and tocotrienols. Methods of making tocopherol and tocotrienol derivatives with one to three double bonds in the hydrocarbon tail are described herein.

SUMMARY

Methods of making tocol derivatives with modifications to the hydrocarbon tail to allow more efficient binding and uptake of tocols with unsaturated hydrocarbon tails by the αTTP receptor are provided herein. The derivatives are called tocoflexols to indicate the increased flexibility of the hydrocarbon tail as compared to tocotrienols and differentiate this class of compounds from the tocopherols and tocotrienols. The methods described herein provide a highly economical method of producing tocoflexols and related tocol analogues thereof. As more fully described in International Patent Publication No. WO2011/153353, which is incorporated herein by reference in its entirety, tocoflexols may be used to treat a wide variety of conditions and may be used as an anti-inflammatory, radio-protective agent or antioxidant.

One feature of the method is to use inexpensive partially purified tocotrienol preparations from readily available natural sources as starting materials. Pure tocotrienols are difficult to separate from tocopherols and are expensive. Thus the ability to use a partially purified starting material provides an economic advantage. Pure tocotrienols may also be utilized in the methods provided herein.

In one aspect, a novel and economical synthetic route for tocoflexols of general formula (I) and (II) and analogues thereof of the general formula (III)-(IX) shown below.

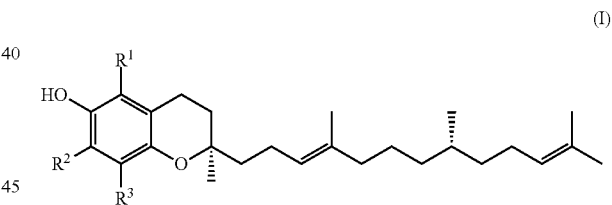

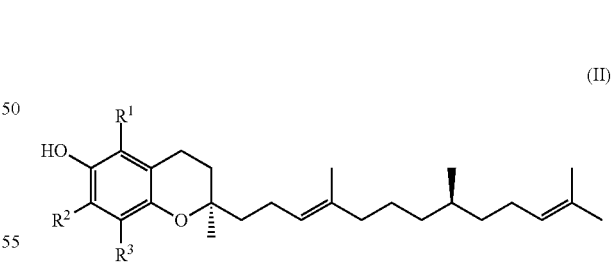

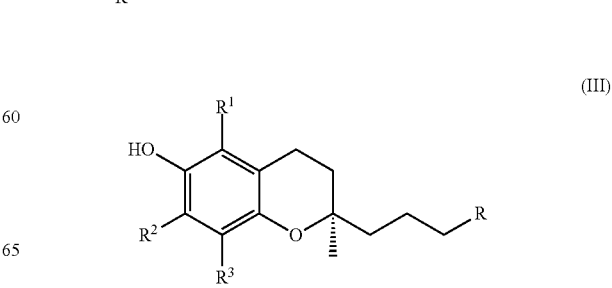

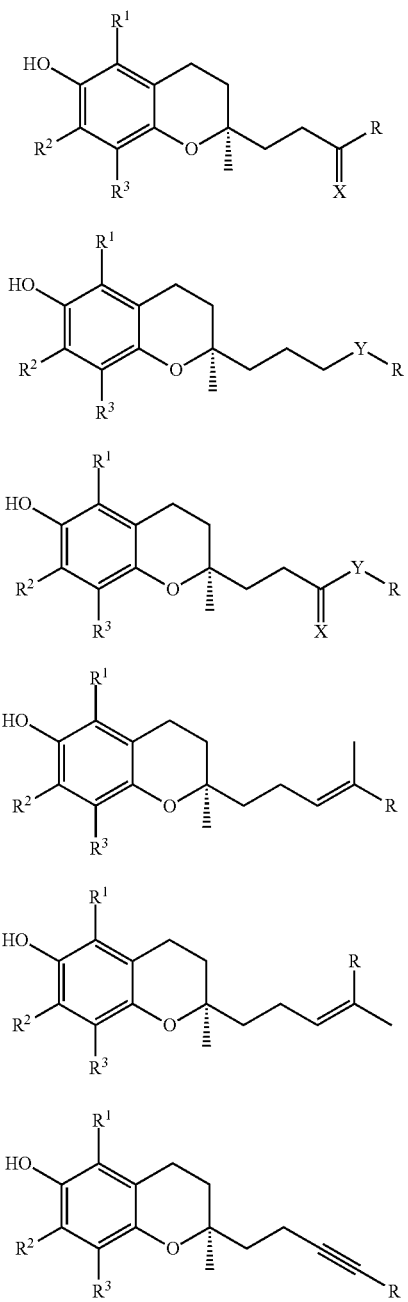

wherein $R^1$, $R^2$, and $R^3$, which can be the same or different, are each selected from hydrogen and methyl; R is hydrogen, straight or branched alkyl of 1-20 carbon atoms, cycloalkyl or substituted cycloalkyl of 3-7 carbon atoms, cycloalkylalkyl or substituted cycloalkylalkyl, alkenyl or substituted alkenyl of 2-20 carbon atoms, alkynyl or substituted alkynyl of 2-20 carbon atoms, aryl or substituted aryl, arylalkyl or substituted arylalkyl, alkylaryl or substituted alkylaryl, arylalkenyl or substituted arylalkenyl, arylalkynyl or substituted arylalkynyl, or heterocyclic or substituted heterocyclic; carbon atoms in the R group can be replaced by one to three of the following atoms or functional groups, which can be same or different: oxygen, nitrogen, sulfur, carbonyl, thiocarbonyl, ester, thioester, thionoester, amide, thioamide, carbamate, thiocarbamate, urea, thiourea, guanidine, $NCH_3$, SO, $SO_2$, $SO_2O$, or $SO_2NH$; X is O, S, NH, or $NCH_3$; Y is O, S, NH, or $NCH_3$.

DETAILED DESCRIPTION

Figure 1:
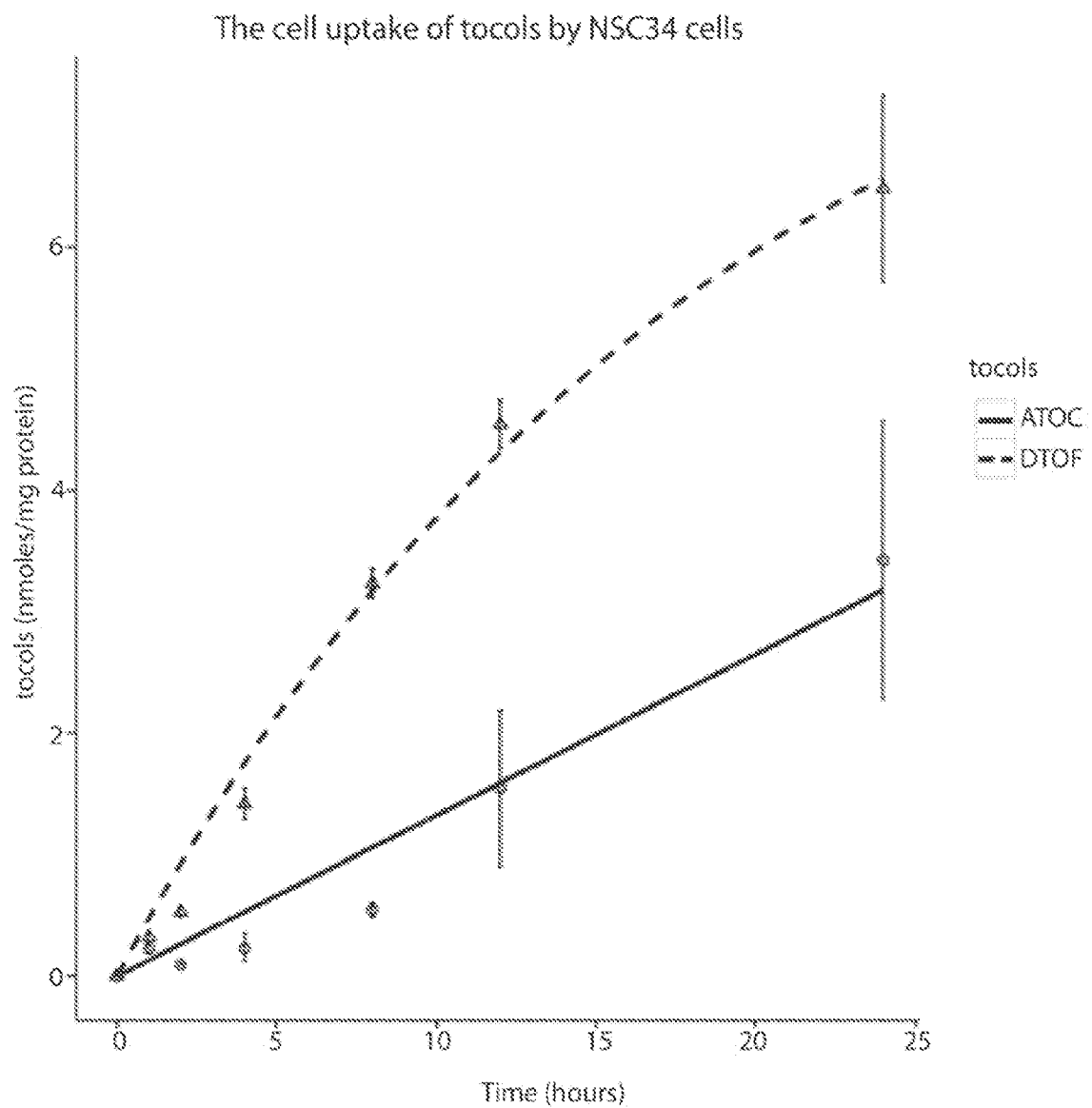
FIG. 1 is a graph showing tocol cell-uptake by mouse NSC 34 cells incubated with 5 mM of α-tocopherol ( . . . ) or δ-tocoflexol ( - - - ).

Processes for making tocoflexols and analogues thereof as shown in formula I-IX above are described herein. The process is markedly attractive from a commercial point of view and affords a simple and highly economical method to synthesize tocoflexols and analogues thereof. The tocoflexols are attractive as they have increased ability to bind αTTP and thus have a longer half-life in the body. The extended half-life of these compounds will facilitate their use by decreasing the number of doses necessary as well as the amount of compound to be administered. It could also produce increased biological activity. Tocoflexols and methods of using the tocoflexols are provided in International Patent Publication No. WO 2011/153353, which is incorporated herein by reference in its entirety. A novel process for making these compounds is provided herein.

Commercially available tocotrienols are purified from natural oils, where they occur as mixtures of tocotrienols and tocopherols. These mixtures are difficult to separate and that makes the pure tocotrienols very expensive. Thus, the fact that our synthetic scheme works effectively using partially purified or pure tocotrienol preparations from natural oils, makes this process commercially feasible. The partially purified tocotrienols can be obtained from sources such as annatto, oat, barely, wheat germ, rice bran, and palms. In the examples, an oil with about 34% tocotrienol was used, but oils with a lower percentage of tocotrienols may be used in the methods. Oils with at least 5%, 10%, 15%, 20%, 25% or 30% of a given tocotrienol will work in the methods described herein.

The process comprises the following steps. The first step (step (a)) is to introduce a protective group to the phenolic OH group of tocotrienols of the formula (X) to form product of the formula (XI):

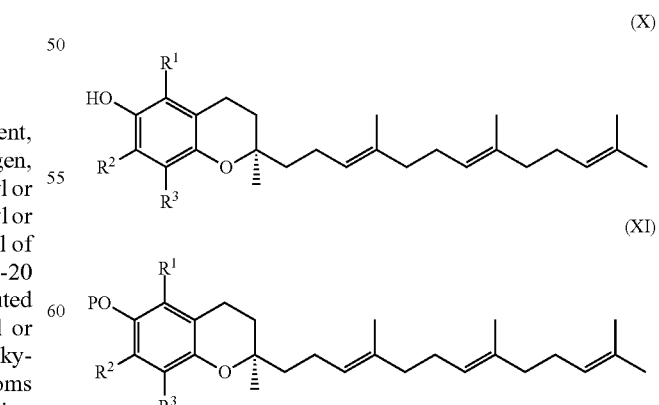

wherein $R^1$, $R^2$, and $R^3$, which can be same or different, are each selected from hydrogen and methyl; P is hydroxyl protective group including but not limited to methyl, methoxymethyl, benzyloxymethyl, 2-(trimethylsilyl)ethoxymethyl, methylthiomethyl, phenylthiomethyl, tetrahydropyranyl, 1-ethoxyethyl, propargyl, t-butyl, benzyl, 4-methoxybenzyl, o-nitrobenzyl, 9-anthrylmethyl, 4-methoxyphenyl, trimethylsilyl, triethylsilyl, triisopropylsilyl, t-butyldimethylsilyl, t-butyldiphenylsilyl, formyl, acetyl, benzoyl, methoxycarbonyl, ethoxycarbonyl, 2,2,2-trichloroethylcarbonyl, benzoxycarbonyl, methanesulfonyl, and toluenesulfonyl.

Suitable solvents for the reaction include all common aprotic solvents. The reaction temperature can range from −20° C., to 120° C., preferably between −5° C. to 25° C. The reaction time can range from 5 minutes to 24 hours, preferably between 30 min to 3 hours.

Tocotrienols (X) can be obtained from natural sources, such as bran oil, palm oil, and annatto oil. Tocotrienols (X) can be used in pure forms or as crude mixtures.

Step (b) is an oxidative cleavage of double bonds in products from step (a) in the formula (XI) to afford aldehyde intermediate in the formula (XII):

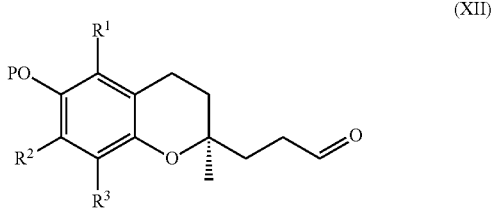

(XII)

wherein $R^1$, $R^2$, $R^3$, and P are the same as described in the first step.

The oxidation is performed using $OsO_4/NaIO_4$. The other common method is ozonolysis. The reaction solvent for $OsO_4/NaIO_4$ reaction is preferably a mixture of tetrahydrofuran and water. Other common ethers such as diethyl ethyl, methyl tert-butyl ether, diisopropyl ether, and 1,4-dioxane mixed with water can also be used. The reaction temperature is preferably below 40° C.

Step (c) is a Horner-Wadsworth-Emmons reaction in which aldehyde of the formula (XII) from step (b) is reacted with trialkyl 2-phosphonopionate (XIII):

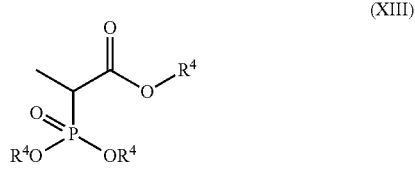

(XIII)

wherein $R^4$ is methyl, ethyl, propyl, isopropyl, or benzyl to afford products of the formula (XIV):

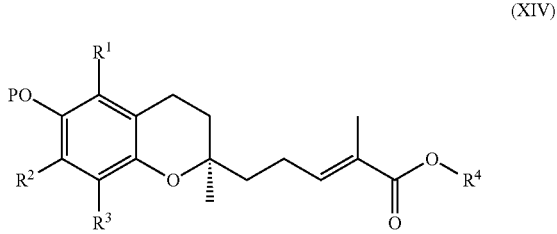

(XIV)

Phosphonopionate (XIII) is initially treated with a base to form ylid. The preferred base is sodium hydride. Other common bases, including but are not limited to potassium hydride, lithium hydride, potassium tert-butoxide, sodium tert-butoxide, lithium tert-butoxide, butyl lithium, lithium diisopropylamide, lithium diethylamide, sodium amide, potassium bis(trimethylsilyl)amide, sodium bis(trimethylsilyl)amide, and lithium bis(trimethylsilyl)amide can also be used. The reaction is running preferably between −78 to 30° C. The reaction time is ranging preferably from 1-12 hours. The reaction is suitably running in tetrahydrofuran. Other suitable solvents, including but not limit to diethyl ether, diisopropyl ether, methyl tert-butyl ether, dimethylformide, and dimethylacetamide, can also be used.

Step (d) is a reaction in which compounds in the formula (XIV) from step (c) are reduced to form compounds in the formula (XV):

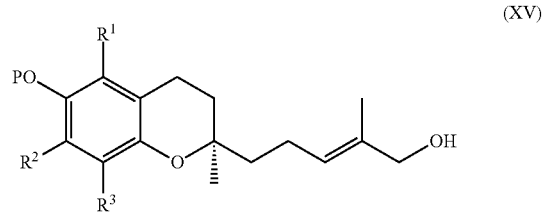

(XV)

The reduction is suitably performed using diisobutylaluminium hydride. Other common reagents, including but not limited to lithium borohydride, lithium triethyl borohydride, borane, lithium aluminium hydride, lithium trimethoxide aluminium hydride, aluminium hydride, lithium aluminium hydride mixed with aluminium chloride, and sodium borohydride mixed with lithium chloride or calcium chloride, can also be used. The reaction is running preferably between −78 to 30° C. The reaction time is ranging preferably from 1-12 hours. The reaction is suitably running in tetrahydrofuran. Other suitable solvents, including but not limit to diethyl ether, diisopropyl ether, and methyl tert-butyl ether, can also be used.

In step (e), a reaction in which the hydroxyl group in compounds in the formula (XV) from step (d) is converted to a leaving group to form compounds in the formula (XVI):

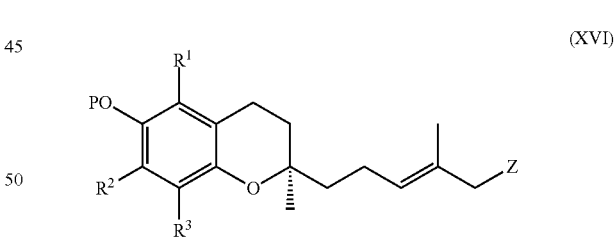

(XVI)

wherein Z is OTs, OMs, OTf($CF_3SO^-$), Cl, or Br.

Step (f) is a coupling reaction between compound in the formula (XVI) from step (e) and a Grignard reagent or an organozinc reagent in the formula (XVII):

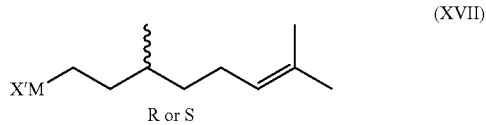

(XVII)

R or S wherein X' is chloro, bromo, or iodo; M is Mg or Zn, to form compound (XVIII) or (XIX):

Finally in step (g), a reaction removing the protective group in compounds in the formula (XVIII) and (XIX) from step (f) to afford the final product in the formula (I) and (II):

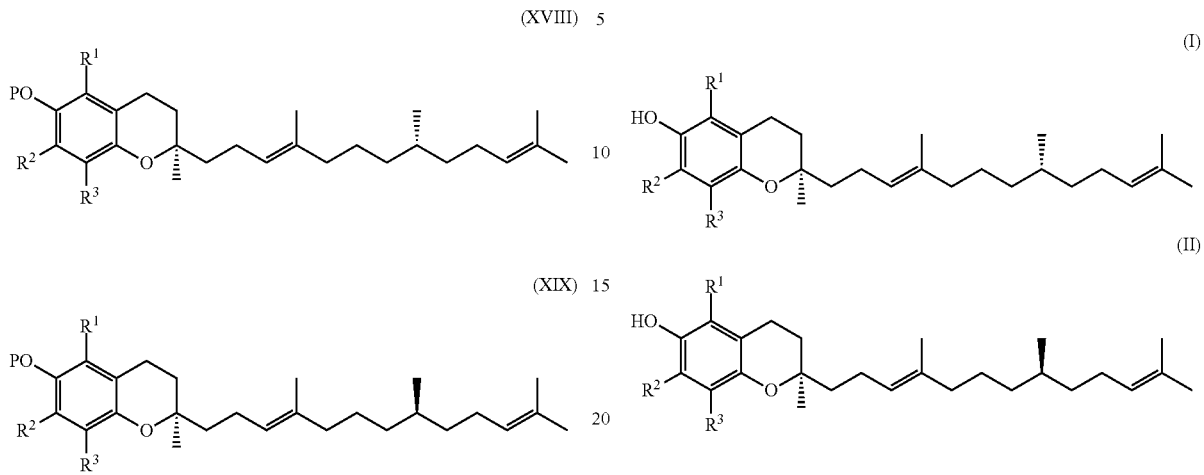

The reaction is catalyzed by a transition metal with or without a ligand. (XVII) is prepared from the corresponding halogenide by standard methodologies.

The reaction is performed by using standard de-protection methodologies.

The overall embodiment of the process adopted for the preparation of tocoflexols of the formula (I) and (II) is depicted in the flow chart (Scheme 1) shown below:

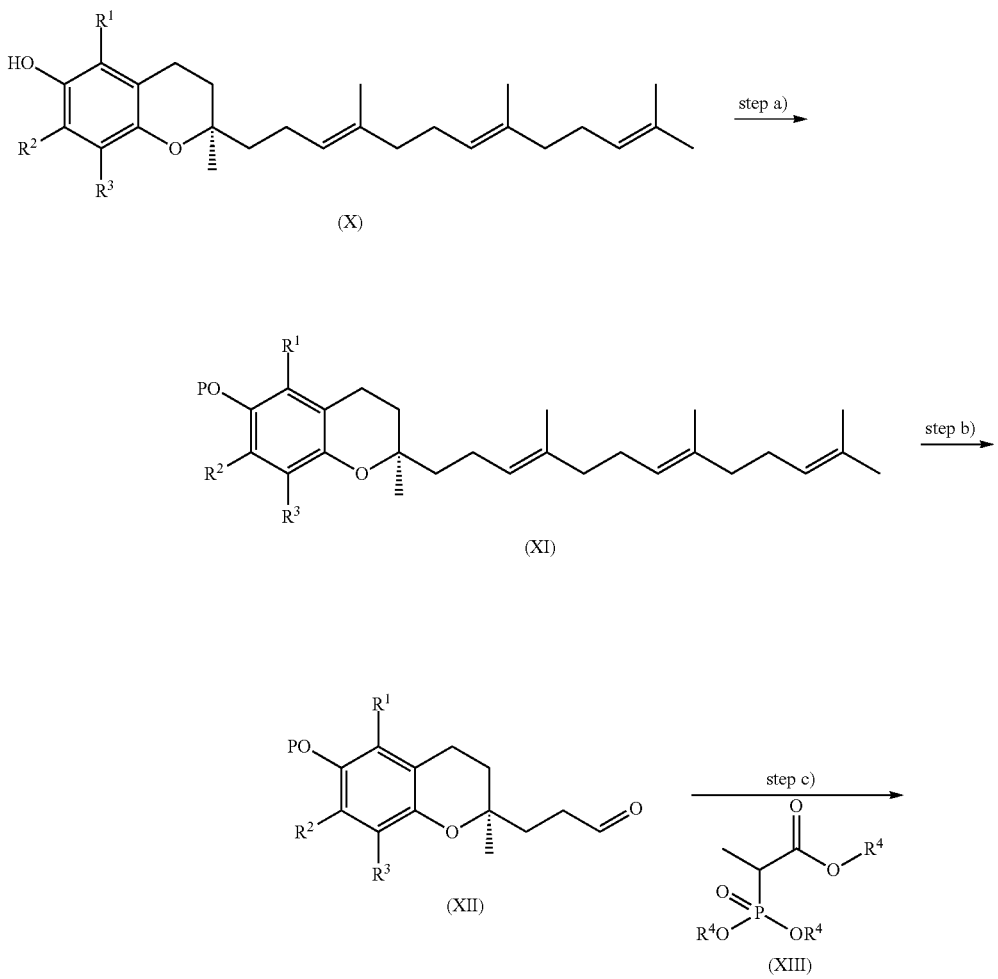

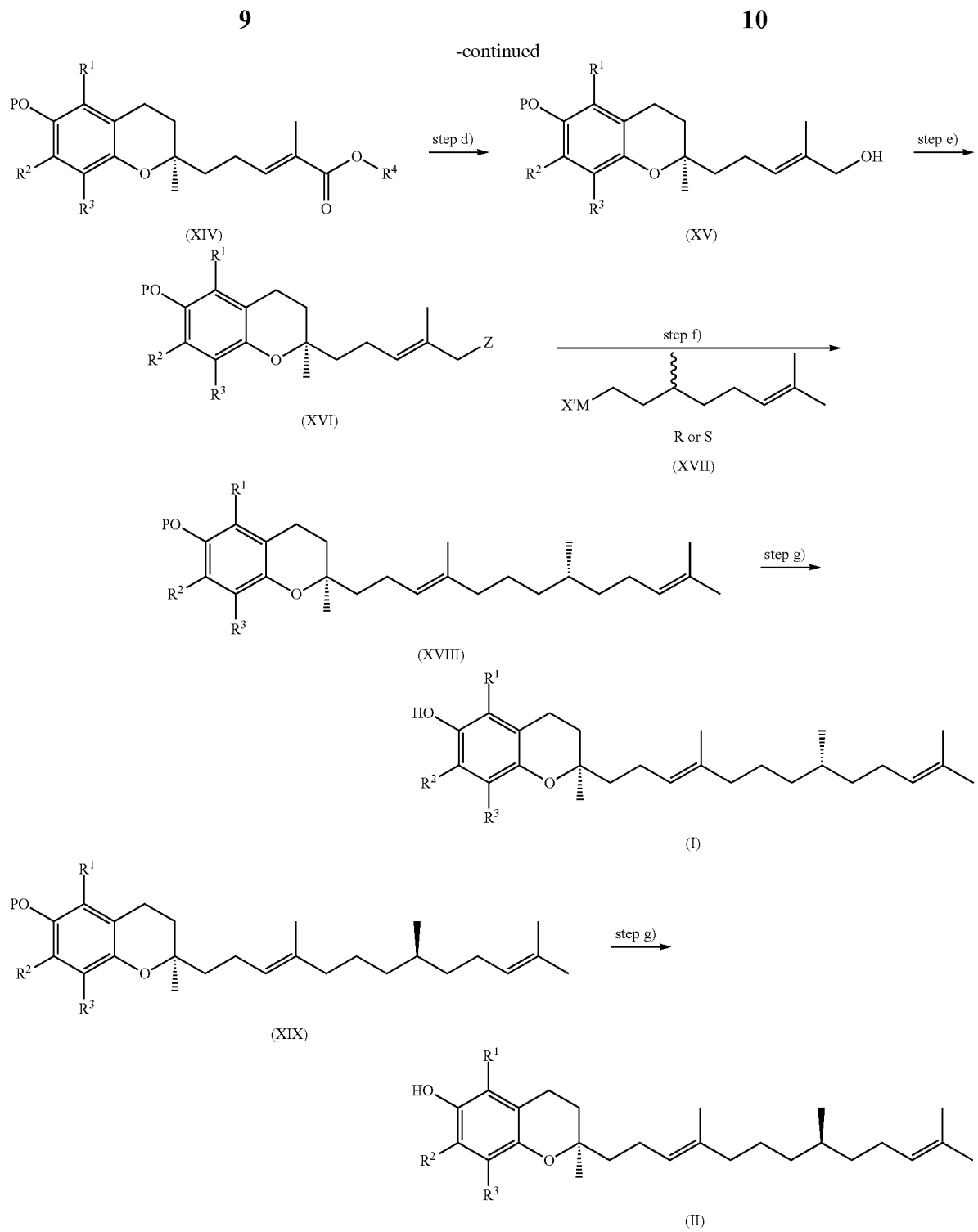

"Hydroxy-protecting group" as used herein refers to a substituent that protects hydroxyl groups against undesirable reactions during synthetic procedures such as those O-protecting groups disclosed in Greene and Muts, "Protective Groups In Organic Synthesis," (John Wiley & Sons, New York, 3$^{rd}$ edition, 1999). Hydroxy-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl: tetrahydropyranyl ethers; substituted ethyl ethers, for example, 2,2,2-trichloroethyl; silyl ethers, for example, trimethylsilyl, t-butyl-dimethylsilyl and t-butyldiphenylsilyl: and esters, for example, acetate, propionate, benzoate and the like.

"Alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms ($C_{1-20}$alkyl), suitably 1 to 10 carbon atoms ($C_{1-10}$ alkyl), preferably 1 to 8 carbon atoms ($C_{1-8}$ alkyl), more preferably 1 to 6 carbon atoms (C$_{1-4}$ alkyl), and even more preferably 1 to 4 carbon atoms (C$_{1-4}$ alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like.

"Alkenyl" as used herein alone or as part of a group refers to monovalent hydrocarbon radicals having a straight or branched hydrocarbon chains having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl and the like.

"Alkynyl" as used herein alone or as part of a group refers to monovalent hydrocarbon radicals having a straight or branched hydrocarbon chains having one or more triple bonds and containing from 2 to about 10 carbon atoms, more preferably from 2 to about 5 carbon atoms. Examples of alkynyl radicals include ethynyl, propynyl, (propargyl), butynyl and the like.

"Aryl" as used herein, alone or as part of a group, includes an organic radical derived from an aromatic hydrocarbon by removal of one hydrogen, and includes monocyclic and polycyclic radicals, such as phenyl, biphenyl, naphthyl.

"Alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy and the like.

"Cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl and the like.

"Cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups. "Unsubstituted" means that the carbon chain or ring contains no other substituents other than carbon and hydrogen.

"Branched" means that the carbon chain is not simply a linear chain. "Unbranched" means that the carbon chain is a linear carbon chain.

"Saturated" means that the carbon chain or ring does not contain any double or triple bonds. "Unsaturated" means that the carbon chain or ring contains at least one double bond. An unsaturated carbon chain or ring may include more than one double bond.

"Hydrocarbon group" means a chain of 1 to 25 carbon atoms, suitably 1 to 12 carbon atoms, more suitably 1 to 10 carbon atoms, and most suitably 1 to 8 carbon atoms. Hydrocarbon groups may have a linear or branched chain structure. Suitably the hydrocarbon groups have one branch.

"Carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, suitably 4 to 7 carbon atoms, and more suitably 5 to 6 carbon atoms in the ring. Bicyclic carbocyclic groups contain 8 to 12 carbon atoms, preferably 9 to 10 carbon atoms in the rings.

"Heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

"Heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

"Silyl" as used herein refers to a silicon atom optionally substituted by one or more alkyl, aryl and aralkyl groups.

"Isomer". "isomeric form", "stereochemically isomeric forms" or "stereoisomeric forms", as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

The following examples are meant only to be illustrative and are not meant as limitations on the scope of the invention or of the appended claims. All references cited herein are hereby incorporated by reference in their entireties.

EXAMPLES

Example 1

Preparation of Tert-Butyldimethylsilyl Protected δ-Tocotrienol

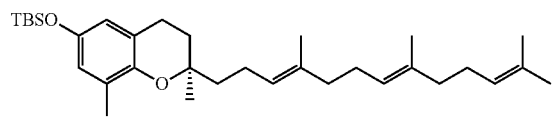 [SMILES: CC(C)=CCC/C(C)=C/CC/C(C)=C/CC[C@]1(C)CCc2cc(O[Si](C)(C)C(C)(C)C)cc(C)c2O1]

A crude mixture of δ-tocotrienol was obtained from annatto oil. The mixture contains about 34% of δ-tocotrienol.

The mixture also contains γ-tocotrienol, approximately in a 1:10 ratio to δ-tocotrienol. To a solution of 6.35 g of this mixture CH$_2$Cl$_2$ (30 mL) was added imidazole (2.73 g, 40.10 mmol). TBSCl (2.90 g, 19.25 mmol) was added after the mixture was cooled to 0° C. The resulting mixture was stirred at room temperature overnight. Ethylacetate (120 mL) was added, and washed with water (50 mL) and saturated saline (50 mL). Organic phases were combined and then dried over Na$_2$SO$_4$, filtered and evaporated to dryness. The residue was purified by silica gel column chromatography (hexanes/ethylacetate 50:1) to afford 3.81 g partially purified yellow oil. The major components in the oil were TBS protected δ-tocotrienol and γ-tocotrienol in a ratio of 10 to 1 according to GC-MS. The resulting oil is carried forth and used in the next step as such.

Example 2

Preparation of (S)-3-(6-(tert-butyldimethylsilyloxy)-2,8-dimethylchroman-2-yl)propanal

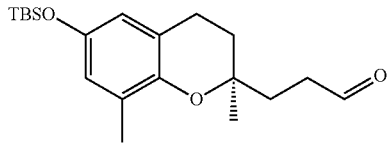 [SMILES: Cc1cc(O[Si](C)(C)C(C)(C)C)cc2c1O[C@](C)(CCC=O)CC2]

To a solution of the yellow oil obtained from example 1 (1.76 g) in TH/H$_2$O (3:1, 80 mL) was added OsO$_4$ (43 mg, 0.17 mmol, 5 mol %) and then NaIO$_4$ (8.86 g, 41.4 mmol). The mixture was stirred at room temperature for 24 hours. Ethylacetate (100 mL) and water (100 mL) was added. Aqueous phase was extracted with ethylacetate (2×50 mL) and combined organic phases were washed with water (50 mL) and saturated saline (50 mL), and then dried over Na$_2$SO$_4$, filtered and evaporated to dryness. The resulting oil is carried forth and used in the next step as such.

Example 3

Preparation of (R)-ethyl 5-(6-(tert-butyldimethylsilyloxy)-2,8-dimethylchroman-2-yl)-2-methylpent-2(E)-enoate

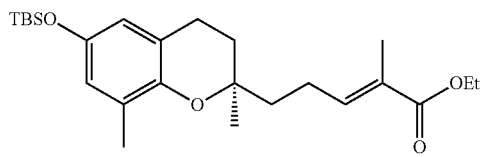 [SMILES: CCOC(=O)/C(C)=C/CC[C@]1(C)CCc2cc(O[Si](C)(C)C(C)(C)C)cc(C)c2O1]

To a solution of triethyl-2-phosphonopionate (822 mg, 3.45 mmol) in THF (15 mL) was added lithium bis(trimethylsilyl)amide (1.0 M in THF, 4.14 mL, 4.14 mmol) drop-wise at 0° C. After 20 min, crude product from example 2 in THF (5 mL) was added drop-wise and reaction was continued overnight at room temperature. Saturated aqueous NH$_4$Cl solution was added. Aqueous phase was extracted with ethylacetate (30 mL). Organic phases were combined and then dried over Na$_2$SO$_4$, filtered and evaporated to dryness. The residue was purified by silica gel column chromatography to afford 250 mg colorless oil. GC-MS 446 (M$^+$). According to GC-MS analysis, the product contains desired product, its Z isomer, E and Z isomers from γ-tocotrienol, and an unknown product. The resulting oil is carried forth and used in the next step as such. Small amount of sample was purified for NMR analysis. $^1$H NMR (400 MHz) CDCl$_3$ 6.70 (dt, J=7.2, 1.6 Hz, 1H), 6.39 (d, J=2.8 Hz, 1H), 6.29 (d, J=2.8 Hz, 1H), 4.17 (q, J=7.2 Hz, 2H), 2.70 (m, 2H), 2.32 (q, J=8.0 Hz, 2H), 2.11 (s, 3H), 1.82 (s, 3H), 1.76 (m, 2H), 1.63 (m, 2H), 1.28 (t, J=7.2 Hz, 3H), 1.27 (s, 31), 0.97 (s, 9H), 0.16 (s, 6H) ppm; GC-MS 432 (M$^+$).

Example 4

Preparation of (R)-5-(6-(tert-butyldimethylsilyloxy)-2,8-dimethylchroman-2-yl)-2-methylpent-2(E)-en-1-ol

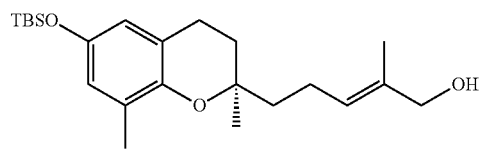 [SMILES: C/C(=C\CC[C@]1(C)CCc2cc(O[Si](C)(C)C(C)(C)C)cc(C)c2O1)CO]

DIBAL-H (1.0 M in toluene, 3.47 mL, 3.47 mmol) was added drop-wise to a solution of (R)-ethyl 5-(6-(tert-butyldimethylsilyloxy)-2,8-dimethylchroman-2-yl)-2-methylpent-2(E)-enoate (250 mg, 0.58 mmol) in CH$_2$Cl$_2$ (10 mL) at −78° C. After 4 h, the reaction was quenched by slowly adding MeOH. Then saturated Rochelle's salt (30 mL) was added and stirred overnight. The aqueous phase was extracted with ethyacetate (30 mL×3). Organic phases were combined and then dried over Na$_2$SO$_4$, filtered and evaporated to dryness. The residue was purified by silica gel column chromatography to afford 142 mg colorless oil in pure form. $^1$H NMR (400 MHz) CDCl$_3$ 6.45 (d, J=2.4 Hz, 1H), 6.36 (d, J=2.4 Hz, 1H), 5.42 (t, J=7.2 Hz, 1H), 3.97 (s, 2H), 2.68 (m, 2H), 2.17 (q, J=8.0 Hz, 2H), 2.11 (s, 3H), 1.64 (s, 3H), 1.76 (m, 2H), 1.66 (m, 1H), 1.57 (m, 1H), 1.45 (br s, 1H), 0.97 (s, 9H), 0.16 (s, 6H) ppm; $^{13}$C NMR (100 MHz) CDCl$_3$ 147.8, 146.4, 135.0, 127.0, 126.4, 121.0, 120.3, 117.4, 75.3, 69.1, 39.5, 31.7, 25.9, 24.2, 22.6, 22.0, 18.3, 16.3, 13.7, −4.3 ppm; GC-MS 390 (M$^+$).

Example 5

Preparation of (R)-5-(6-(tert-butyldimethylsilyloxy)-2,8-trimethylchroman-2-yl)-2-methylpent-2(E)-enyl p-toluenesulfonate

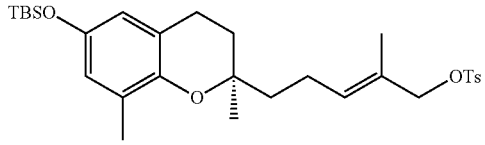 [SMILES: C/C(=C\CC[C@]1(C)CCc2cc(O[Si](C)(C)C(C)(C)C)cc(C)c2O1)COS(=O)(=O)c1ccc(C)cc1]

Et$_3$N (109 mg, 1.08 mmol), pTsCl (82 mg, 0.43 mmol), and DMAP (5 mg) were added to a solution of (R)-5-(6-(tert-butyldimethylsilyloxy)-2,8-dimethylchroman-2-yl)-2-methylpent-2(E)-en-1-ol (142 mg, 0.36 mmol) in CH$_2$Cl$_2$ (3 mL) at 0° C. Warmed to room temperature, and stirred overnight. Ethylacetate (20 mL) was added and washed with water and saturated saline. Organic phase was dried over Na₂SO₄, filtered and evaporated to dryness. The resulting light yellow oil is carried forth and used in the next step as such.

Example 6

Preparation of TBS Protected (2R,8'S)-δ-tocoflexol

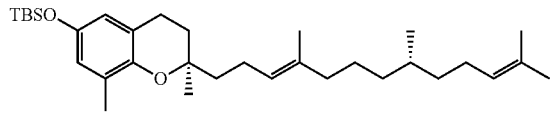 [SMILES: CC(C)=CCC[C@@H](C)CCC/C(C)=C/CC[C@]1(C)CCc2cc(O[Si](C)(C)C(C)(C)C)cc(C)c2O1]

(R)-Citronellyl magnesium bromide in THF was added dropwise to a suspension of CuI (190 mg, 1 mmol) in THF (1 mL) at −40° C. After stirred for 15 min at the same temperature, (R)-5-(6-(tert-butyldimethylsilyloxy)-2,8-dimethyl-chroman-2-yl)-2-methylpent-2(E)-enyl p-toluenesulfonate from example 5 in THF (4 mL) was added drop-wise. After 10 min stirring at the same temperature, the reaction mixture was slowly warmed to room temperature and then stirred overnight. Saturated aqueous NH₄Cl solution was added. Aqueous phase was extracted with ethyacetate (20 mL×2). Organic phases were combined and then dried over Na₂SO₄, filtered and evaporated to dryness. The residue was purified by silica gel column chromatography to afford 118 mg TBS protected (2R,8'S)-δ-tocoflexol as colorless oil. Yield 64% (two steps). ¹H NMR (400 MHz) CDCl₃ 6.45 (s, 1H), 6.36 (s, 1H), 5.05-5.15 (m, 2H), 2.68 (t, J=: 6.4 Hz, 2H), 2.11 (s, 3H), 2.05-2.16 (m, 2H), 1.86-2.03 (m, 4H), 1.73 (m, 2H) 1.68 (s, 3H), 1.00-1.65 (m, 9H), 1.60 (s, 3H), 1.57 (s, 31H), 1.25 (s, 3H), 1.00 (s, 9H), 0.85 (d, J=6.0 Hz, 3H), 0.16 (s, 6H) ppm; ¹³C NMR (100 MHz) CDCl₃ 147.8, 146.6, 135.7, 131.2, 127.1, 125.3, 124.3, 121.1, 120.3, 117.4, 75.5, 40.2, 40.0, 37.3, 36.8, 32.6, 31.7, 26.0, 25.9, 25.6, 24.3, 22.7, 22.4, 19.8, 18.4, 17.9, 16.3, 16.0, −4.2 ppm; GC-MS 512 (M⁺).

Example 7

Preparation of (2R,8'S)-δ-tocoflexol

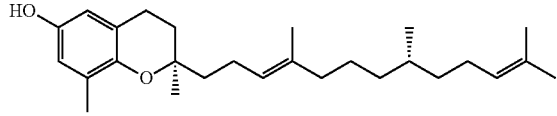 [SMILES: CC(C)=CCC[C@@H](C)CCC/C(C)=C/CC[C@]1(C)CCc2cc(O)cc(C)c2O1]

TBAF (30 mg, 0.094 mmol) was added to a solution of TBS protected (2R,8'S)-5-tocoflexol (12 mg, 0.023 mmol) in THF. The reaction mixture was stirred for 3 hr at room temperature. 9 mg colorless oil was obtained after purification. Yield 97%. ¹H NMR (400 MHz) CDCl₃ 6.47 (s, 1H), 6.38 (s, 1H), 5.05-5.15 (m, 2H), 4.16 (s, 1H), 2.63-2.75 (m, 2H), 2.13 (s, 3H), 2.07-2.16 (m, 2.1), 1.85-2.01 (m, 4H), 1.75 (m, 2H) 1.68 (s, 3H), 1.00-1.65 (m, 91H), 1.60 (s, 3H), 1.58 (s, 3H), 1.26 (s, 3H), 0.85 (d, J=6.0 Hz, 3H) ppm; ¹³C NMR (100 MHz) CDCl₃ 147.9, 146.3, 135.8, 131.2, 127.6, 125.3, 124.3, 121.5, 115.8, 112.8, 75.6, 40.2, 40.0, 37.3, 36.8, 32.6, 31.6, 25.9, 25.8, 25.6, 24.3, 22.7, 22.4, 19.8, 17.9, 16.3, 16.0 ppm; GC-MS 398 (M⁺).

Example 8

Preparation of Tert-Butyldimethylsilyl Protected γ-Tocotrienol

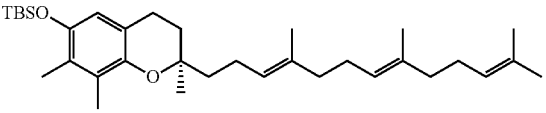 [SMILES: CC(C)=CCC/C(C)=C/CC/C(C)=C/CC[C@]1(C)CCc2cc(O[Si](C)(C)C(C)(C)C)c(C)c(C)c2O1]

To a solution of γ-tocotrienol (0.99 g, 2.41 mmol) in CH₂Cl₂ (10 mL) was added imidazole (410 mg, 6.03 mmol). TBSCl (436 mg, 2.89 mmol) was added after the mixture was cooled to 0° C. The resulting mixture was stirred at room temperature overnight. Ethylacetate (40 mL) was added, and washed with water (20 mL) and saturated saline (20 mL). Organic phases were combined and then dried over Na₂SO₄, filtered and evaporated to dryness. The residue was purified by silica gel column chromatography (hexanes/ethylacetate 50:1) to afford 1.20 g light yellow oil. Yield 95%. ¹H NMR (400 MHz) CDCl₃ 6.39 (s, 1H), 5.12-5.23 (m, 3H), 2.72 (m, 1H), 2.08-2.22 (m, 5H), 2.15 (s, 3H), 2.14 (s, 3H), 1.98-2.04 (m, 41H), 1.58-1.88 (m, 2H), 1.72 (s, 3H), 1.64 (s, 9H), 1.30 (s, 3H), 1.06 (s, 9H), 0.22 (s, 6H) ppm; ¹³C NMR (100 MHz) CDCl₃ 146.3, 146.0, 135.2, 135.1, 131.4, 126.4, 125.8, 124.68, 124.66, 124.6, 124.5, 117.8, 116.0, 115.9, 75.3, 40.0, 39.9, 31.7, 27.0, 26.8, 26.14, 26.10, 25.9, 24.3, 24.2, 22.6, 22.4, 18.5, 17.9, 16.22, 16.21, 16.08, 16.07, −4.02, −4.04 ppm; (GC-MS 524 (M⁺).

Example 9

Preparation of (S)-3-(6-(tert-butyldimethylsilyloxy)-2,7,8-trimethylchroman-2-yl)propanal

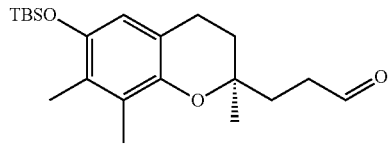 [SMILES: Cc1c(O[Si](C)(C)C(C)(C)C)cc2c(c1C)O[C@](C)(CCC=O)CC2]

To a solution of tert-butyldimethylsilyl protected γ-tocotrienol (637 mg, 1.21 mmol) in THF/H₂O (2:1, 48 mL) was added OsO₄ (15.4 mg, 5 mol %) and then NaIO₄ (3.03 g). The mixture was stirred at room temperature for 24 hours. Ethylacetate (100 mL) was added, and washed with water (50 mL) and saturated saline (50 mL). Organic phases were combined and then dried over Na₂SO₄, filtered and evaporated to dryness. The resulting light yellow oil (600 mg) is carried forth and used in the next step as such. GC-MS 362 (M⁺).

Example 10

Preparation of (R)-ethyl 5-(6-(tert-butyldimethylsilyloxy)-2,7,8-trimethylchroman-2-yl)-2-methylpent-2(E)-enoate

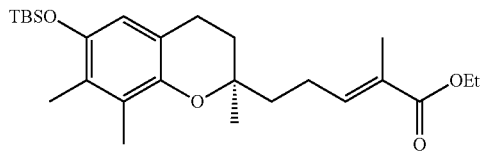 [SMILES: CCOC(=O)/C(C)=C/CC[C@]1(C)CCc2cc(O[Si](C)(C)C(C)(C)C)c(C)c(C)c2O1]

Triethyl-2-phosphonopionate (48 mg, 0.20 mmol) was added slowly to a suspension of NaH (60%, 8.4 mg) in THF (2 mL) at room temperature. After 5 min, the reaction was cooled to 0° C. Crude aldehyde (55 mg) from example 2 in THF (1 mL) was added drop-wise and reaction was continued for 30 min at 0° C., then 1 h at room temperature. Saturated aqueous NH$_4$Cl solution was added. Aqueous phase was extracted with ethyacetate (10 mL). Organic phases were combined and then dried over Na$_2$SO$_4$, filtered and evaporated to dryness. The residue was purified by silica gel column chromatography to afford 12 mg colorless oil. Yield 12% (two steps). GC-MS 446 (M$^+$).

The reaction gave an E/Z ratio of 13:1. In a similar reaction, when Lithium bis(trimethylsilyl)amide was used as base, the E/Z was 6:1.

Example 11

Preparation of (R)-5-(6-(tert-butyldimethylsilyloxy)-2,7,8-trimethylchroman-2-yl)-2-methylpent-2(E)-en-1-ol

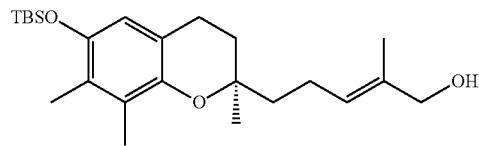 [SMILES: C/C(=C\CC[C@]1(C)CCc2cc(O[Si](C)(C)C(C)(C)C)c(C)c(C)c2O1)CO]

DIBAL-H was added dropwise to a solution of (R)-ethyl 5-(6-(tert-butyldimethylsilyloxy)-2,7,8-trimethylchroman-2-yl)-2-methylpent-2(E)-enoate (37 mg, 0.083 mmol) in CH$_2$Cl$_2$ (2 mL) at −78° C. After 1 h. the reaction was quenched by slowly adding MeOH. Then saturated Rochelle's salt (5 mL) was added and stirred overnight. The aqueous phase was extracted with ethyacetate (10 mL×3). Organic phases were combined and then dried over Na$_2$SO$_4$, filtered and evaporated to dryness. The residue was purified by silica gel column chromatography to afford 30 mg colorless oil. Yield 89%. GC-MS 446 (M$^+$).

Example 12

Preparation of (R)-5-(6-(tert-butyldimethylsilyloxy)-2,7,8-trimethylchroman-2-yl)-2-methylpent-2(E)-enyl p-toluenesulfonate

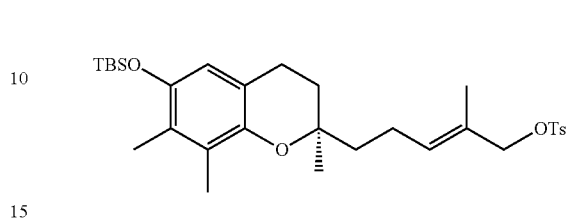

Et$_3$N (5 mg), pTsCl (4 mg), and DMAP (one small piece) were added to a solution of (R)-5-(6-(tert-butyldimethylsilyloxy)-2,7,8-trimethylchroman-2-yl)-2-methylpent-2(E)-en-1-ol (7 mg, 0.017 mmol) in CH$_2$Cl$_2$ (1 mL) at 0° C. Warmed to room temperature, and stirred overnight. Ethylacetate (2 mL) was added and washed with water and saturated saline. Organic phase was dried over Na$_2$SO$_4$, filtered and evaporated to dryness. The resulting light yellow oil (600 mg) is carried forth and used in the next step as such.

Example 13

Preparation of TBS Protected (2R,8'R)-γ-Tocoflexol

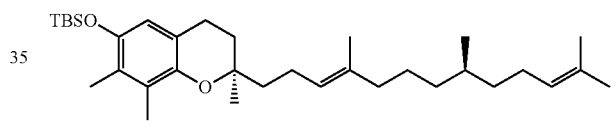

(S)-Citronellyl magnesium bromide in THF was added dropwise to a suspension of CuI in THF (0.5 mL) at −40° C. After stirred for 15 min at the same temperature, (R)-5-(6-(tert-butyldinmethylsilyloxy)-2,7,8-trimethylchroman-2-yl)-2-methylpent-2(E)-enyl p-toluenesulfonate from example 5 in THF (1 mL) was added dropwise. After 10 min stirring at the same temperature, the reaction mixture was slowly warmed to room temperature and then stirred overnight. Saturated aqueous NH$_4$Cl solution was added. Aqueous phase was extracted with ethyacetate (5 mL×2). Organic phases were combined and then dried over Na$_2$SO$_4$, filtered and evaporated to dryness. The residue was purified by silica gel column chromatography to afford about 2 mg product. GC-MS 526 (M$^+$).

Example 14

Preparation of (2R,8'R)-γ-Tocoflexol

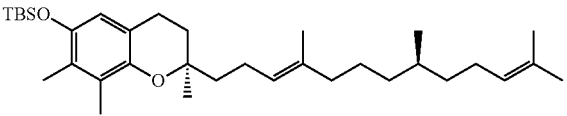 [SMILES: CC(C)=CCC[C@H](C)CCC/C(C)=C/CC[C@]1(C)CCc2cc(O[Si](C)(C)C(C)(C)C)c(C)c(C)c2O1]

TBAF was added to a solution of TBS protected (R,R)-γ-tocoflexol (about 1 mg) in THF. The reaction mixture was stirred for 2 h at room temperature. The reaction was completed according to TLC and GC-MS. GC-MS 412 (M⁺).

Example 15

Cell Uptake of Tocoflexols

There is consistent evidence that the cell-uptake rate of the vitamin E components strongly correlates with their bioactivity. This has been clearly observed for their hypocholesterolemic, cytoprotective, and anticancer activities as reported in McIntyre et al. (2000) Lipids 35(2): 171-180; Nowak et al. (2012) J Pharmacol Exp Ther 340(2):330-338; Qureshi et al. (1991) 53(4 Suppl): 1021S-1026S: Rasool et al. (2006) J Nutr Sci Vitaminol 52(6):473-478; and Rasool et al. (2008) Arch Pharm Res 31(9): 1212-1217.

Thus, to evaluate the potential bioactivity of the tocoflexols, we compared its cell-uptake of a representative tocoflexol, δ-tocoflexol (DTOF) that of α-tocopherol (AT), and found that DTOF has a cell-uptake almost double that that of ATOC (FIG. 1). The experiment was carried out as described below.

Cell Culture:

Mouse NSC 34 cells were grown in Dulbecco's modified Eagle's medium (DMEM) supplemented with 10% fetal bovine serum and 1% penicillin/streptomycin at 37° C. in a humidified atmosphere containing 95% air and 5% CO2. The cell culture medium was replaced every 2 or 3 days with fresh medium containing serum and antibiotic. Cells were reseeded when the cell monolayers became confluent. For the experiments, cells at passages 15-27 were seeded in 6-well plates at 1 million cells per well.

Incubation/Treatment of NSC 34 Cells with Tocols:

5 mM test solutions were prepared in DMSO. NSC 34 monolayers above 80% confluency were treated with 2 µl of test compound (final concentration 5 µM) for 0, 1, 2, 4, 8, 12, and 24 hours. In a 6 well plate, the upper 3 wells were used for the measurement of tocols and lower 3 wells were used for protein extraction.

Extraction of Tocols from NSC 34 Cells:

After respective period of treatment, the media were removed and cells and washed twice with ice-cold phosphate-buffered saline (PBS 1×). Following the washing, NSC 34 cells were scrapped and suspended in 1 ml ice cold PBS in a 1.5 ml microcentrifuge tube. Cells were spun down at 1,000 g for 2 min and the supernatant was discarded and pellet was suspended in 0.5 ml 95% ice-cold methanol and respective internal standard was added. We added internal standards in order to correct for minor variations occurring during sample preparation and analysis. Mixture was sonicated followed by extraction with 0.5 ml hexane using vigorous vortexing and spinning at 500 g for 2 min. Extraction process was repeated twice and hexane layer was collected in a glass vial. Hexane extracts were dried under nitrogen and were quantitatively transferred to a deactivated glass micro insert using methylene chloride and dried under nitrogen. Samples were derivatized using N-methyl-N-TMS-trifluoroacetamide and injected in GC/MS for the analysis.

Protein Extraction:

The media were removed and cells were washed twice with ice-cold phosphate-buffered saline (PBS 1×). Following the washing. NSC 34 cells were scrapped and suspended in 100 µl ice cold RIPA buffer added with protease inhibitor in a 1.5 ml micro centrifuge tube. Cells were centrifuged at 14,000 rpm for 15 min at 4° C. Supernatant was collected in 1.5 ml micro centrifuge tube and stored at −20° C. if assay is not performed on the same day.

Protein Assay:

Protein concentration was determined using the Pierce BCA protein assay kit.

GC/MS:

The derivatized samples were analyzed using GC/MS by single ion monitoring (Agilent 5975 GC/MSD; Agilent Technologies, Palo Alto, Calif.). The GC was equipped with a 30-m HP-5MS column (0.250 mm, 0.25 µm). Samples were analyzed using helium as the carrier gas (head pressure of 27 psi), 1 µl splitless injection, the injector temperature was 275° C., the column temperature was maintained at 220° C. for 2 min followed by a gradient of 25° C./min to 300° C., and remained at that temperature for 10 min. The transfer line temperature was maintained at 285° C. for 13.5 min followed by a gradient of 25° C./min to 300° C., and remained at that temperature for 10 min. The MS conditions were: electron impact, source temperature 230° C., quadrupole temperature 150° C., and ionization voltage 70 eV.

Example 16

Ability of the Tocoflexols to Inhibit Lipid Peroxidation

Figure 2:
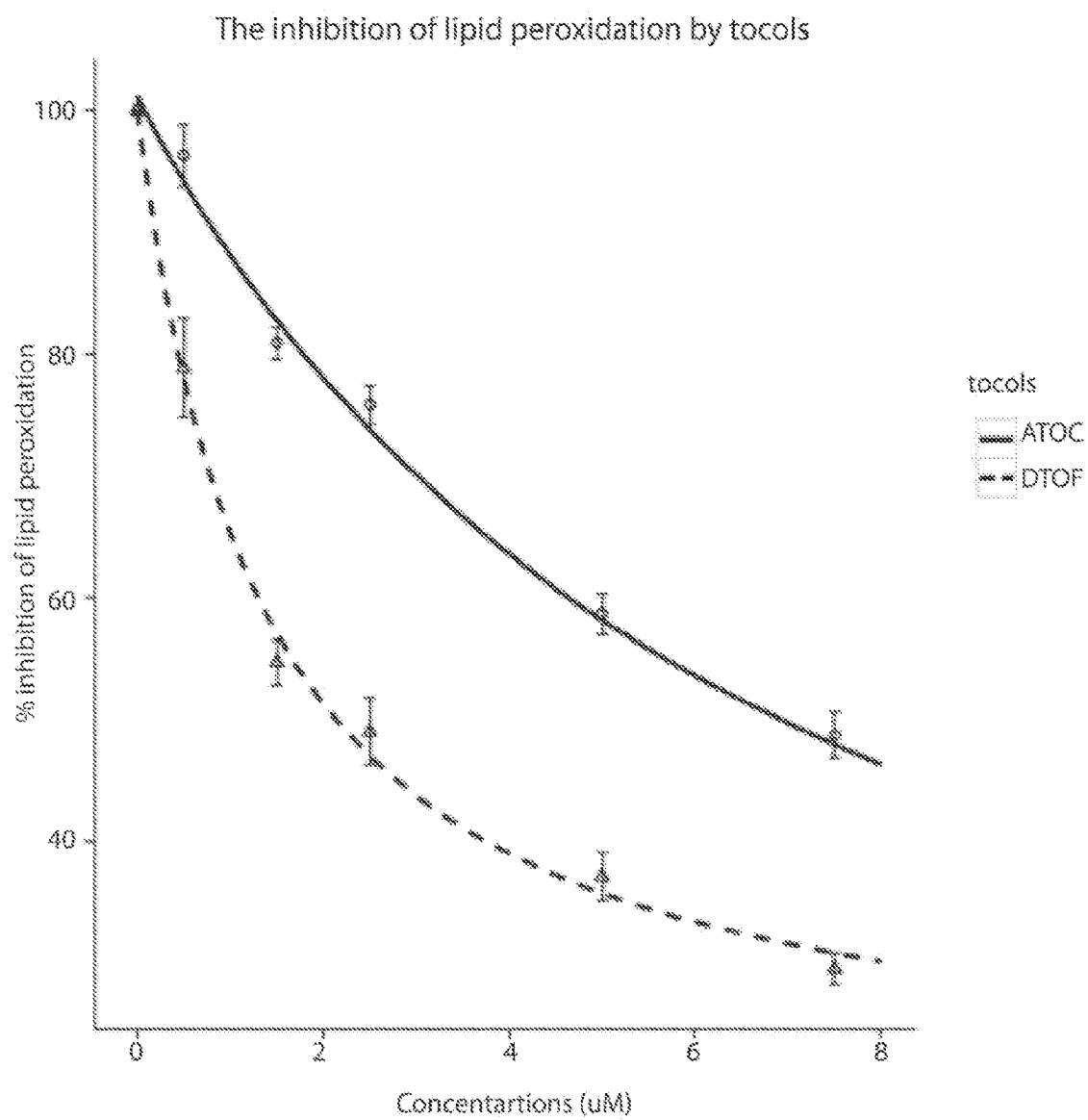
FIG. 2 is a graph showing that δ-tocoflexol is 5 times more potent as an antioxidant than α-tocopherol.

One of the most well-known properties of the vitamin E components is their ability to prevent lipid peroxidation. See Traber et al. (2011) Free Radis Biol Med 51(5):1000-1013. Briefly, the antioxidant activity of vitamin E analogs was evaluated in rat liver microsomes by measuring inhibition of lipid peroxidation after TBHP (thiobarbituric acid reactive substance) treatment. Wistar rat liver microsomes (BD Biosciences) were diluted in phosphate buffer, 0.1 M (pH 7.4), at the final protein concentration of 1 mg/ml. The microsomes were treated with different concentrations of tocols (diluted with DMSO) and incubated at 37° C. for 1 hour before inducing lipid peroxidation with 200 µM TBHP (DMSO) for 30 min. In the assay for the inhibition of peroxidation of rat liver microsomes treated with 200 µM TBHP, δ-tocoflexol showed an antioxidant potential ($IC_{50}$=1.35 µM) more of 5 times of that of AT ($IC_{50}$=6.78 µM) (FIG. 2). These results support the notion that δ-tocoflexol will have a potent bioactivity when tested in vivo.

What is claimed is:

1. A method of making tocoflexols of Formula (I) or (II) comprising the steps of:
(a) introducing a protective group to the phenolic hydroxyl group of a pure or partially purified tocotrienol of formula (X) to form the product of formula (XI); wherein the solvent used is an aprotic solvent, the reaction temperature is between −20° C. to 120° C. and the reaction time can range from 5 minutes in 24 hours:

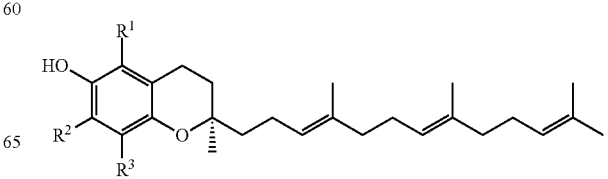

(X)

-continued (XI)

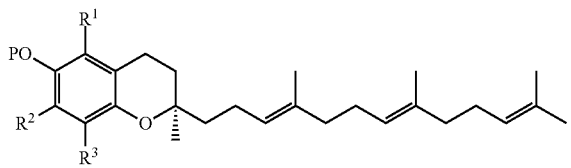

wherein $R^1$, $R^2$, and $R^3$, are the same or different and are each selected from hydrogen and methyl and P is hydroxyl protective group; and (b) cleaving by oxidation the double bonds in products from step (a) in the formula (XI) to afford an aldehyde intermediate in the formula (XII); wherein the oxidation is performed using $OsO_4/NaIO_4$ or ozonolysis:

(XII)

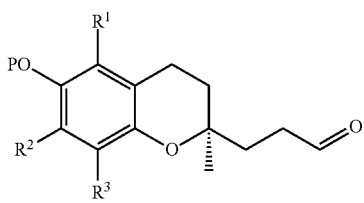

wherein $R^1$, $R^2$, $R^3$, and P are the same as described in step (a);

(c) reacting the aldehyde of the formula (XII) from step (b) with trialkyl 2-phosphonopionate (XIII); wherein the reaction is a Horner-Wadsworth-Emmons reaction; wherein the phosphonopionate (XIII) is initially treated with a base selected from the group consisting of sodium hydride, potassium hydride, lithium hydride, potassium tert-butoxide, sodium tert-butoxide, lithium tert-butoxide, butyl lithium, lithium diisopropylamide, lithium diethylamide, sodium amide, potassium bis(trimethylsilyl)amide, sodium bis(trimethylsilyl)amide, and lithium bis(trimethylsilyl)amide:

(XIII)

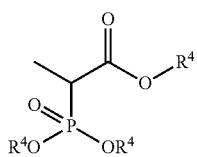

wherein $R^4$ is independently methyl, ethyl, propyl, isopropyl, or benzyl to afford products of the formula (XIV):

(XIV)

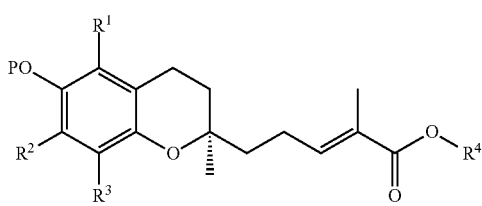

(d) reducing the compounds obtained from step (c) to form compounds of formula (XV) using diisobutylaluminum hydride, lithium borohydride, lithium triethyl borohydride, borate, lithium aluminium hydride, lithium trimethoxide aluminium hydride, aluminium hydride, lithium aluminium hydride mixed with aluminium chloride, and sodium borohydride mixed with lithium chloride or calcium chloride:

(XV)

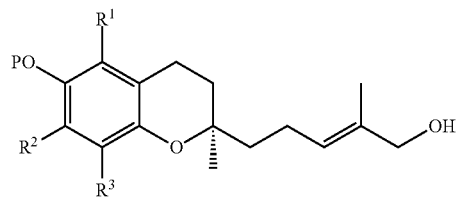

(e) converting the hydroxyl group in the compounds from step (d) to a leaving group to form compounds of the formula (XVI):

(XVI)

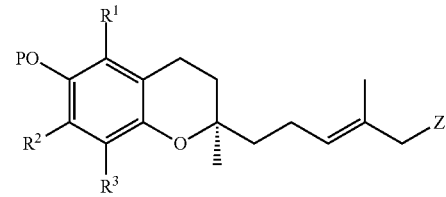

wherein Z is OTs, OMs, OTf, Cl, or Br;

(f) performing a coupling reaction between the compounds obtained in step (e) and a Grignard reagent or an organozinc reagent in the formula (XVII), wherein the reaction is catalyzed by a transition metal with or without a ligand:

(XVII)

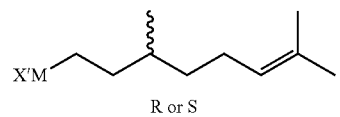

R or S wherein X' is chloro, bromo, or iodo; and M is Mg or Zn, to form compound (XVIII) or (XIX);

(XVIII)

-continued

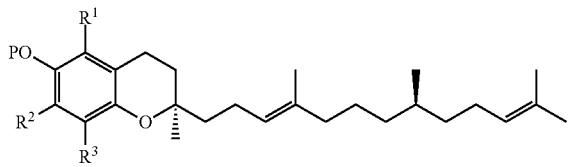

(XIX)

(g) removing the protective group in compounds in the formula (XVIII) and (XIX) from step (f) to afford the final product in the formula (I) and (II):

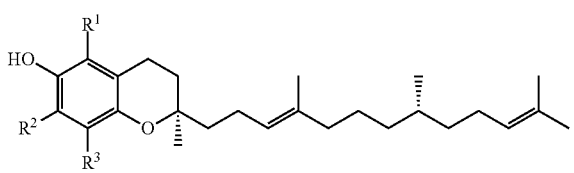

(I)

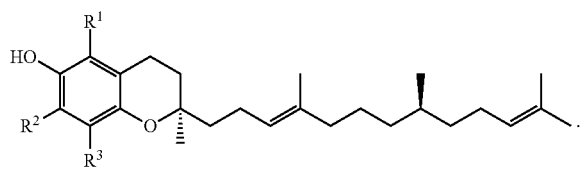

(II)

2. The method of claim 1, wherein the protective group of step (a) is selected from methyl, methoxymethyl, benzyloxymethyl, 2-(trimethylsilyl)ethoxymethyl, methylthiomethyl, phenylthiomethyl, tetrahydropyranyl, 1-ethoxyethyl, propargyl, t-butyl, benzyl, 4-methoxybenzyl, o-nitrobenzyl, 9-anthrylmethyl, 4-methoxyphenyl, trimethylsilyl, triethylsilyl, triisopropylsilyl, t-butyldimethylsilyl, t-butyldiphenyisilyl, formyl, acetyl, benzoyl, methoxycarbonyl, ethoxycarbonyl, 2,2,2-trichloroethylcarbonyl, benzoxycarbonyl, methanesulfonyl, and toluenesulfonyl.

3. The method of claim 1, wherein the tocotrienols of formula (I) are from bran oil, palm oil, and annatto oil.

4. The method of claim 1, wherein the oxidation in step (b) is performed using $OsO_4/NaIO_4$.

5. The method of claim 4, wherein the reaction solvent used in step (b) for $OsO_4/NaIO_4$ reaction is a mixture of tetrahydrofuran, diethyl ethyl, methyl tert-butyl ether, diisopropyl ether, or 1,4-dioxane with water.

6. The method of claim 1, wherein the oxidation in step (b) is performed by ozonolysis.

7. The method claim 1, wherein the reaction temperature in step (b) is below 40° C.

8. The method of claim 1, wherein the reaction is maintained between −78 to 30° C. during step (c) and/or during step (d) for between 1-12 hours.

9. The method of claim 1, wherein the solvent used in step (c) and/or in step (d) is selected from tetrahydrofuran, diethyl ether, diisopropyl ether, methyl tert-butyl ether, dimethylformide, and dimethylacetamide.

10. The method of claim 2, wherein P is t-butyldimethylsilyl; and wherein the reaction temperature for step (a) is between −5° C. and 25° C. and the reaction time for step (a) is between 30 min and 3 hours.

11. The method of claim 10, wherein the oxidation in step (b) is performed using $OsO_4/NaIO_4$ in a solvent comprising tetrahydrofuran and water at a reaction temperature below 40° C.

12. The method of claim 11, wherein the base of step (c) is sodium hydride.

13. The method of claim 12, wherein step (d) is performed using diisobutylaluminium hydride; and wherein the reaction temperature of step (d) is between −78° C. and 30° C. and the reaction time of step (d) is between 1 and 12 hours.

* * * * *